United States Patent [19]

Walker

[11] Patent Number: 4,871,731

[45] Date of Patent: Oct. 3, 1989

[54] CAPTOPRIL AND DILTIAZEM COMPOSITION AND THE LIKE

[75] Inventor: Steven D. Walker, Kansas City, Mo.

[73] Assignee: Marion Laboratories, Inc., Kansas City, Mo.

[21] Appl. No.: 105,244

[22] Filed: Oct. 7, 1987

[51] Int. Cl.⁴ .................. A61K 31/40; A61K 31/55
[52] U.S. Cl. ................................. 514/211; 514/423
[58] Field of Search ........................... 514/211, 423

[56] References Cited

U.S. PATENT DOCUMENTS

| | | | |
|---|---|---|---|
| 3,562,257 | 2/1971 | Kugita et al. | 260/293.3 |
| 4,046,889 | 9/1977 | Ondetti et al. | 424/244 |
| 4,369,172 | 1/1983 | Schor et al. | 424/19 |
| 4,376,767 | 3/1983 | Sloan | 424/232 |
| 4,420,628 | 12/1983 | Inoue et al. | 560/17 |
| 4,438,035 | 3/1984 | Gaino et al. | 260/239.3 B |
| 4,440,740 | 4/1984 | Fix et al. | 424/1.1 |
| 4,520,112 | 5/1987 | Snyder | 436/504 |
| 4,555,398 | 11/1985 | Oda | 424/19 |
| 4,555,503 | 11/1985 | Patchett | 514/19 |
| 4,557,934 | 12/1985 | Cooper | 424/128 |
| 4,584,294 | 4/1986 | Ruyle | 514/214 |
| 4,605,550 | 8/1986 | Trill | 424/22 |
| 4,605,552 | 8/1986 | Fritschi | 424/45 |
| 4,634,716 | 1/1987 | Parsons et al. | 514/423 |
| 4,654,372 | 3/1987 | Marcoux | 514/646 |
| 4,666,705 | 5/1987 | DeCrosta et al. | 424/482 |
| 4,694,002 | 9/1987 | Floyd et al. | 514/211 |
| 4,748,239 | 5/1988 | Floyd et al. | 540/523 |
| 4,752,645 | 6/1988 | Das et al. | 540/523 |

FOREIGN PATENT DOCUMENTS 8140787 5/1988 Australia .
2607004 5/1988 France .
2178314 2/1987 United Kingdom .

OTHER PUBLICATIONS

Tomita et al., *Kekvu to Junkan,* 33(10), 1257-64, (1985), 1-14, Engl. Translation.
Guazzi et al., *Circulation,* 70(2), 279-84, (1984).
Brouwer et al., *J. Cardiovasc. Pharmacol,* 7(Suppl. 1), S88-91, (1985).
Abramowicz et al., *The Medical Letter ® on Drugs & Therapeutics,* 26(Issue 676), 107-12, (1985).
Cushman et al., *Biochemistry,* 16, 5484-91, (1977).
Hawley (Ed.) *The Condensed Chemical Dictionary, 10th Edition,* 1039 (1981).
Huff et al., (Eds.), *Physicians' Desk Reference, 41st Edition,* 1173-74, 1940-45, (1987).
Eudragit (TM) RL&S Technical Literature, Rohm Pharma.
Zema et al., *Clin. Res.,* 34(2), 409A, (1986).
Zema et al., *Br. Heart J.,* 58, 512-17, (Nov. 1987).
Zema, *Clin. Res.,* 32(3), 686A, (1984).

*Primary Examiner*—Allen J. Robinson
*Attorney, Agent, or Firm*—Christopher J. Rudy; Neal O. Willmann

[57] ABSTRACT

A combination of the titled compounds, appropriate salt(s) thereof, and/or the like, is employed for significantly alleviating hypertension and so forth.

25 Claims, No Drawings

CAPTOPRIL AND DILTIAZEM COMPOSITION AND THE LIKE

FIELD

This invention concerns a method of use of such a pharmaceutical composition as one which involves a combination of such compounds as a benzothiazepine derivative and an azetidine-2-carboxylic acid derivative with a pharmaceutical composition therefor and a process for its preparation. The method and composition are generally useful, among other things, treatment of hypertension, and the process can prepare the composition.

BACKGROUND

Treatment of hypertension and associated disorders may be undertaken with the aid of various drugs. Among such drugs are included inhibitors of angiotensin-converting enzyme, so-called ACE-inhibitors, beta-andrengenic blockers, so-called betablockers, and calcium ion influx inhibitors, so called calcium antagonists, and often includes the use of diuretics. Certain combinations from among such types of drugs may be employed.

However, hypertension and associated disorders have a relatively poorly understood etiology. Thus, the treatment thereof is generally undertaken empirically.

SUMMARY

The present invention includes, in one aspect, a method for treating hypertension which comprises concurrently administering a combination of such an ACE-inhibitor as captopril with such a calcium antagonist as diltiazem or pharmaceutically acceptable salts thereof. Another aspect includes a composition of matter comprising said ACE-inhibitor with said calcium antagonist. A further aspect can include a process for preparing the composition of the invention which comprises incorporating said ACE-inhibitor with said calcium antagonist under conditions such that the composition is prepared.

The method and composition aspects of the invention are especially useful for treatment of hypertension. Notably, these aspects can provide control of hypertension which is often of a significantly greater magnitude than that control provided by either one of said ACE-inhibitor or said calcium antagonist. Thus, these aspects can provide unexpectedly dramatic control of hypertension especially for many difficult to treat patients suffering from same. Further, these aspects may significantly improve renal function in certain patients to levels which are improved beyond those which one would expect said ACE-inhibitor or said calcium antagonist to alone provide. The process for preparing the composition aspect thus provides one possibility for such treatment.

DETAILED DESCRIPTION

The ACE-inhibitors of the invention are well known, and same can be commercially obtained or can be prepared by known processes. One such process is that of Ondetti et al., U.S. Pat. No. 4,046,889 (Sept. 6, 1977). Said Ondetti et al. patent is incorporated herein by reference.

Preferred of the ACE-inhibitors of the invention is captopril. Captopril is 1-(3-mercapto-1-methyl-2-oxo-propyl)-L-proline.

The calcium antagonists of the invention are well known, and same can be commercially obtained or can be prepared by known processes. One such process is that of Kugita et al., U.S. Pat. No. 3,562,257 (Feb. 9, 1971). Other processes include those of Inoue et al., United States Patent 4,420,628 (Dec. 13, 1983), and Gaino et al., United States Patent 4,438,035 (Mar. 20, 1984). Said Kugita et al., Inoue et al. and Gaino et al. patents are incorporated herein by reference.

Preferred of the calcium antagonists of the invention is diltiazem, especially the pharmaceutically acceptable monohydrochloride salt thereof. Diltiazem is (+)-cis-3-(acetyloxy)-5-[2-(dimethylamino)ethyl]2,3-dihydro-2-(4-methoxyphenyl)-1,5-benzothiazepin-4(5H)one.

The composition of the invention can be formulated with generally any amount of the ACE-inhibitor of the invention and any amount of the calcium antagonist of the invention. Suitable amounts more typically include weight ratios of the calcium antagonist of the invention to the ACE-inhibitor of the invention generally ranging from about 2:1 to about 3:1, desirably, about 2.4:1.

The composition of the invention can be prepared into any suitable pharmaceutically administrable form, to include intravenous and oral dosage forms, by known methods. Oral dosage forms, for example, capsules, tablets, syrups, dragees, and the like, are especially advantageous.

Desirably, in connection with the oral dosage forms, the calcium antagonist of the invention is in embodied in a sustained release form. This sustained release form is desirably made to release substantially all of the calcium antagonist of the invention within a day or less. A twice daily dose (BID) is convenient. The dosage release is desirably designed to be a substantially linear release of the calcium antagonist of the invention. For example, about 90 percent by weight of the calcium antagonist of the invention, which is available in the inventive combination herein and/or which can be administered by the inventive method herein, is suitably released in about 12 to 15 or 16 hours, with generally the same amount per hour of the calcium antagonist of the invention being generally released throughout this period from the initial time of administration.

In order to accomplish this, methods known in the art can be employed. For example, nonpareil round sugar seeds approximately 0.5 mm in diameter can be coated with an appropriate wax by coating from a wax and isopropanol mixture, the isopropanol portion being next evaporated, by conventional methods. Following this, the wax-coated sugar seeds are mixed with a powder which contains, or exclusively is, the calcium antagonist of the invention, again, by conventional methods, say, in a stainless steel coating pan. At this stage, a desirable result can include such drug-coated beads as containing, say, about 49 percent by weight of the sugar seed, with about 1 percent by weight of the bead being the wax, and the remainder being the calcium antagonist of the invention. Next, these drug coated beads are placed into an air suspension coater such as the well-known Glatt air suspension coater, commonly referred to as a "Wurster coater." There, the drug-coated beads are fluidized by air, and a spray coating of a suitable polymer film is generally applied thereto by misting or spraying. The misting or spraying generally employs a solvent for the polymer, and the solvent is in general subsequently evaporated therefrom. The suitable polymer film can be an acrylic polymer film, for example, a Eudragit ™ (Rohm-Pharma) film. Desirably, the Eudragit ® which is employed therein is a mixture of about 5 percent of the RL variety and about 95 percent of the RS variety, and about from 9 to 35 percent by weight of the polymer coated bead is the polymer. The polymer film coated bead sample advantageously contains a bimodal distribution of the polymer film coated beads, with about half or so having about from 12 to 17.5 percent by weight of the final polymer coated bead being the polymer, and the remaining portion having about from 20 to 30 percent by weight of the final polymer coated bead being the polymer.

The following example further illustrates the invention. So-called monotherapy portions thereof are intended for comparative purposes, with the combination therapy being especially illustrative of the present invention.

EXAMPLE WITH COMPARATIVE

Diltiazem hydrochloride (Marion Laboratories, Inc.) was formed into Eugradit ™ film coated beads in a Wurster coater. The beads which were coated thereby contain about 49 percent by weight nonpareil sugar seeds with a diameter of about 0.5 mm, about 1 percent by weight wax and about 50 percent by weight of the diltiazem hydrochloride coated thereon from a powder. The Eudragit ™ film coated beads had a bimodal distribution with approximately half of them having about from 12 to 17.5 percent by weight of the polymer film coating therewith, and the remaining ones having about from 20 to 30 percent by weight of the polymer film coating therewith. These sustained release beads are tableted. Also employed is tributyl citrate or acetyl tributyl citrate.

Captopril was obtained and employed as CAPOTEN ® tablets (E.R. Squibb & Sons, Inc.).

A study was conducted with human subjects (patients) who manifested mild to moderate hypertension. A single-blind baseline phase of 4-6 weeks was used in order to establish that each patient had a resting supine diastolic blood pressure (DBP) between 95 and 114 mmHg, inclusive. Eligible patients were randomized into one of two treatment groups: diltiazem, i.e., the diltiazem hydrochloride as tableted above, or captopril. An eight-week, double-blind optional titration period orally administered to the patients diltiazem at 120, 240, or 360 mg/day, while doses of captopril were 50, 100, and 150 mg/day. DBP goal response was defined as either:

1. A DBP less than 90 mmHg for patients with a baseline greater than or equal to 100 mmHg, or
2. A decrease in DBP of at least 10 mmHg for patients with a baseline between 95 and 99 mmHg, inclusive.

The eight weeks of monotherapy was followed by eight additional weeks during which combination therapy is undertaken by having the opposite medication titrated using the oral doses noted above for the patients who have not exhibited the DBP goal response.

For the monotherapy, the study was conducted with 199 patients, who were randomized for receiving either diltiazem or aptopril, with 113 as the number of patients actively evaluable for efficacy. During this monotherapy period, patients receiving diltiazem had mean decreases in DBP of 5.3, 7.5, 8.7, and 10.7 mmHg at Weeks 2, 4, 6, and 8, respectively. Patients receiving captopril at the same time points exhibited mean decreases of 6.8, 6.8, 7.4, and 8.0, respectively.

The percentage of patients who exhibited the DBP goal response during the monotherapy was 15 percent, 28 percent, 32 percent, and 39 percent for diltiazem at Weeks, 2, 4, 6, and 8, respectively. The corresponding percentages for captopril were 23 percent, 25 percent, 32 percent, and 37 percent.

For the combination therapy, the diltiazem with captopril added patients (n=30 to 34) exhibited mean decreases in DBP of 7.7, 9.7, 11.3, and 12.8 mmHg at Weeks 10, 12, 14, and 16, respectively. The captopril with diltiazem added patients (n=31 to 33) exhibited comparable decreases of 6.2, 5.5, 6.5, and 5.6 mmHg at those respective weeks.

The percentage of the diltiazem with captopril added patients who became goal responders was 29 percent, 27 percent, 39 percent, and 47 percent at Weeks 10, 12, 14, and 16, respectively. For the patients receiving captopril with diltiazem added the percentage of goal responders was 24 percent, 15 percent, 47 percent, and 35 percent at the same weeks, respectively.

Mean decrease from baseline in systolic blood pressure (SBP) for patients who were randomized to diltiazem (n=30 to 34) were 3.5, 7.7, 8.1, and 8.7 mmHg at Weeks 2, 4, 6, 8, respectively. For patients who were randomized to captopril, the respective mean decreases were 9.2, 9.2, 10.6, and 9.8 mmHg.

The diltiazem patients having captopril added thereto (n=31 to 33) had means SBP decreases of 7.5, 12.1, 13.0, and 14.5 mmHg at Weeks 10, 12, 14 and 16, respectively. The captopril patients who had diltiazem added thereto (n=31 to 33) exhibited mean SBP decreases of 10.3, 12.9, 13.6, and 13.0.

During the monotherapy, means changes in heart rate varied from −0.6 to −3.8 beats per minute (bpm) for diltiazem and from +0.2 to −2.1 bpm for the patients receiving captopril. During the combination therapy, the diltiazem with captopril patients had mean changes from −1.6 to +0.5 bpm, while the other combination treatment group exhibited a mean change of −2.5 to +3.0 bpm.

These data suggest that both monotherapies were associated with comparable (with the possible exception of Week 8) decreases in DBP of 5 to 11 mmHg, with about from 16 percent to 39 percent of patients achieving goal response. Patients that received combination therapy (generally non-responders to the monotherapy) experienced mean decreases in DBP of 8 to 13 mmHg with about from 15 percent to 47 percent reaching goal response.

More detailed data are shown in the following tables. In the tables, "N" represents the number of appropriately identified patients and "SD" represents the standard deviation from the mean (MEAN) value which is exhibited for those N patients.

TABLE I

| | DILTIAZEM (DTZ) | | | | CAPTOPRIL (CAP) | | | |
| --- | --- | --- | --- | --- | --- | --- | --- | --- |
| | N | MEAN | SD | RESPONDERS | N | MEAN | SD | RESPONDERS |
| Baseline MONOTHERAPY Week 2 | 60 | 99.8 | 4.0 | — | 53 | 99.4 | 4.4 | — |

TABLE I-continued

|  | DILTIAZEM (DTZ) | | | | CAPTOPRIL (CAP) | | | |
| --- | --- | --- | --- | --- | --- | --- | --- | --- |
|  | N | MEAN | SD | RESPONDERS | N | MEAN | SD | RESPONDERS |
| Change from baseline | 60 | −5.3 | 5.3 | 15% | 53 | −6.8 | 6.1 | 23% |
| No. Pts: Lo Dose = 120/50 | 60 | | | | 53 | | | |
| Week 4 | | | | | | | | |
| Change from baseline | 60 | −7.5 | 6.3 | 28% | 53 | −6.8 | 6.5 | 25% |
| No. Pts: Lo Dose = 120/50 | 11 | | | | 12 | | | |
| Mid Dose = 240/100 | 49 | | | | 40 | | | |
| WEEK 6 | | | | | | | | |
| Change from baseline | 60 | −8.7 | 6.4 | 32% | 53 | −7.5 | 6.4 | 32% |
| No. pts: Lo Dose = 120/50 | 5 | | | | 9 | | | |
| Mid Dose = 240/100 | 17 | | | | 6 | | | |
| High Dose = 360/150 | 38 | | | | 38 | | | |
| Week 8 | | | | | | | | |
| Change from baseline | 60 | −10.7 | 7.3 | 39% | 53 | −8.0 | 7.1 | 37% |
| No. Pts: Lo Dose = 120/50 | 2 | | | | 7 | | | |
| Mid Dose = 240/100 | 17 | | | | 5 | | | |
| High Dose = 360/150 | 40 | | | | 40 | | | |
| COMBINATION THERAPY | DILTIAZEM + CAP | | | | CAPTOPRIL + DTZ | | | |
| Week 10 | | | | | | | | |
| Change from baseline | 34 | −7.7 | 6.9 | 29% | 33 | −8.2 | 6.2 | 24% |
| Week 12 | | | | | | | | |
| Change from baseline | 33 | −9.7 | 6.3 | 27% | 33 | −9.1 | 5.5 | 15% |
| Week 14 | | | | | | | | |
| Change from baseline | 31 | −11.3 | 6.5 | 39% | 32 | −11.9 | 6.5 | 47% |
| Week 16 | | | | | | | | |
| Change from baseline | 30 | −12.8 | 5.5 | 47% | 31 | −11.9 | 5.6 | 35% |

TABLE II

RESTING SUPINE SYSTOLIC BLOOD PRESSURE (mmHg)

|  | N | MEAN | SD | N | MEAN | SD |
| --- | --- | --- | --- | --- | --- | --- |
|  | DILTIAZEM (DTZ) | | | CAPTOPRIL (CAP) | | |
| Baseline | 60 | 153.3 | 14.2 | 53 | 150.0 | 14.3 |
| MONOTHERAPY | | | | | | |
| Week 2 | | | | | | |
| Change from baseline | 60 | −3.5 | 8.6 | 52 | −5.1 | 9.2 |
| Week 4 | | | | | | |
| Change from baseline | 60 | −7.7 | 9.1 | 53 | −6.5 | 9.2 |
| Week 6 | | | | | | |
| Change from baseline | 60 | −8.1 | 11.7 | 53 | −9.3 | 10.6 |
| Week 8 | | | | | | |
| Change from baseline | 60 | −8.7 | 11.7 | 53 | −9.2 | 9.8 |
| COMBINATION THERAPY | DILTIAZEM + CAP | | | CAPTOPRIL + DTZ | | |
| Week 10 | | | | | | |
| Change from baseline | 34 | −7.5 | 10.3 | 33 | −10.3 | 9.4 |
| Week 12 | | | | | | |
| Change from baseline | 33 | −12.1 | 11.9 | 33 | −12.9 | 10.1 |
| Week 14 | | | | | | |
| Change from baseline | 31 | −13.0 | 11.0 | 32 | −13.6 | 10.2 |
| Week 16 | | | | | | |
| Change from baseline | 30 | −14.5 | 10.7 | 31 | −13.0 | 9.0 |

TABLE III

RESTING SUPINE HEART RATE (Beats/Min.)

|  | N | MEAN | SD | N | MEAN | SD |
| --- | --- | --- | --- | --- | --- | --- |
|  | DILTIAZEM (DTZ) | | | CAPTOPRIL (CAP) | | |
| Baseline | 60 | 73.1 | 8.9 | 53 | 74.3 | 9.6 |
| MONOTHERAPY | | | | | | |
| Week 2 | | | | | | |
| Change from baseline | 60 | −0.6 | 8.1 | 53 | +0.2 | 8.4 |
| Week 4 | | | | | | |
| Change from baseline | 60 | −2.8 | 9.6 | 53 | −2.1 | 6.0 |
| Week 6 | | | | | | |
| Change from baseline | 60 | −0.8 | 10.4 | 53 | +0.1 | 8.6 |
| Week 8 | | | | | | |
| Change from baseline | 60 | −3.8 | 9.5 | 53 | −0.4 | 8.9 |
| COMBINATION THERAPY | DILTIAZEM + CAP | | | CAPTOPRIL + DTZ | | |
| Week 10 | | | | | | |
| Change from baseline | 34 | −1.2 | 11.0 | 33 | −2.8 | 8.0 |
| Week 12 | | | | | | |
| Change from baseline | 33 | −1.6 | 10.0 | 33 | −2.5 | 7.1 |
| Week 14 | | | | | | |
| Change from baseline | 30 | −0.4 | 9.5 | 32 | −2.1 | 9.6 |
| Week 16 | | | | | | |

TABLE III-continued

| | RESTING SUPINE HEART RATE (Beats/Min.) | | | | | |
| --- | --- | --- | --- | --- | --- | --- |
| | N | MEAN | SD | N | MEAN | SD |
| Change from baseline | 30 | +0.5 | 9.5 | 31 | −3.0 | 9.1 |

This demonstrates that the inventive combination herein substantially advances the diagnostic options for treating hypertension. Significant results are thus demonstrated for such combination therapy especially in connection with those patients who are generally nonresponsive to these types of monotherapy, also bearing in mind that it is not the general rule that the opposite type of monotherapy alone as otherwise herein is effective in alleviating hypertension, and so forth, in such nonresponsive patients.

CONCLUSION

The captopril and diltiazem composition and the like, with use thereof, and so forth are thus provided. Sundry modifications and adaptations can be made by the artisan and by the routineer pursuant to the instant invention without departing from its true spirit and scope especially as particularly pointed out by the following distinctly claimed subject matter.

What is claimed is:

1. A pharmaceutical composition useful for treating hypertension comprising a mixture of captopril or its pharmaceutically acceptable salt(s) and diltiazem or its pharmaceutically acceptable salt(s) in a ratio of diltiazem or its said salt(s) to captopril or its said salt(s) about from 2:1 to 3:1 by weight.

2. The composition of claim 1, which is in a pharmaceutically acceptable intravenous dosage form.

3. The composition of claim 1, which is in a pharmaceutically acceptable oral dosage form.

4. The composition of claim 3, wherein the diltiazem or its said salt(s) is sustainably releasable in a substantially linear manner in about from 12 hours to a day in a suitable human patient.

5. The composition of claim 4, which is in capsule form.

6. The composition of claim 4, which is in tablet form.

7. The composition of claim 1, 2, 3, 4, 5 or 6, wherein said ratio is about 2.4:1.

8. A pharmaceutical composition useful for treating hypertension comprising a mixture of captopril and diltiazem hydrochloride in a ratio of diltiazem hydrochloride to captopril about from 2:1 to 3:1 by weight.

9. The composition of claim 8, which is in a pharmaceutically acceptable intravenous dosage form.

10. The composition of claim 8, which is in a pharmaceutically acceptable oral dosage form.

11. The composition of claim 10, wherein the diltiazem hydrochloride is sustainably releasable in a substantially linear manner in about from 12 hours to a day in a suitable human patient.

12. The composition of claim 11, which is in capsule form.

13. The composition of claim 11, which is in tablet form.

14. The composition of claim 8, 9, 10, 11, 12 or 13, wherein said ratio is about 2.4:1.

15. A method for treating hypertension which comprises concurrently administering to a hypertensive subject an amount effective to treat hypertension of both captopril or its pharmaceutically acceptable salt(s) and diltiazem or its pharmaceutically acceptable salt(s) in a ratio of diltiazem or its said salt(s)) to captopril or its said salt(s) about from 2:1 to 3:1 by weight.

16. The method of claim 15, wherein the captopril or its said salt(s) is captopril, and the diltiazem or its said salt(s) is diltiazem hydrochloride.

17. The method of claim 15 or 16, wherein the hypertensive subject is a human patient.

18. The method of claim 17, wherein the diltiazem or its said salt(s) is administered in a substantially linear manner.

19. The method of claim 18, wherein the captopril or its said salt(s) and the diltiazem or its said salt(s) are administered together in a pharmaceutically acceptable oral dosage form.

20. The method of claim 17, wherein the human patient had failed to appropriately respond either to captopril or its said salt(s), or to diltiazem or its said salt(s), as monotherapy.

21. The method of claim 15 or 16, wherein said ratio is about 2.4:1.

22. The method of claim 17, wherein said ratio is about 2.4:1.

23. The method of claim 18, wherein said ratio is about 2.4:1.

24. The method of claim 19, wherein said ratio is about 2.4:1.

25. The method of claim 20, wherein said ratio is about 2.4:1.

* * * * *